United States Patent
Sananes et al.

(10) Patent No.: US 10,912,568 B2
(45) Date of Patent: Feb. 9, 2021

(54) INFLATABLE AND DETACHABLE BALLOON, DESIGNED TO BE IMPLANTED IN A BODY CAVITY, ASSOCIATED TREATMENT KIT AND DRAINING METHOD

(71) Applicants: Université de Strasbourg, Strasbourg (FR); Institut National de la Sante et de la Recherche Medicale (Inserm), Paris (FR); Hôpitaux Universitaires de Strasbourg (HUS), Strasbourg (FR); Institut Hospitalo-Universitaire de Strasbourg, Strasbourg (FR); INSTITUT DE RECHERCHE CONTRE LES CANCERS DE L'APPAREIL DIGESTIF, Strasbourg (FR); BS MEDICAL TECH INDUSTRY, Niederroedern (FR)

(72) Inventors: Nicolas Sananes, Strasbourg (FR); Romain Favre, Strasbourg (FR); Joël Leroy, Schiltigheim (FR); Christian Debry, Strasbourg (FR); Christian Goetz, Selestat (FR); Bruno Mutet, Strasbourg (FR); Juan Hernandez, Strasbourg (FR); Bertrand Basch, Soufflenheim (FR); Raymond Basch, Mothern (FR)

(73) Assignees: UNIVERSITÉ DE STRASBOURG, Strasbourg (FR); INSTITUT NATIONAL DE LA SANTE ET DE LA RECHERCHE MEDICALE (INSERM), Paris (FR); HÔPITAUX UNIVERSITAIRES DE STRASBOURG (HUS), Strasbourg (FR); INSTITUT HOSPITALO-UNIVERSITAIRE DE STRASBOURG, Strasbourg (FR); INSTITUT DE RECHERCHE CONTRE LES CANCERS DE L'APPAREIL DIGESTIF, Strasbourg (FR); BS MEDICAL TECH INDUSTRY, Niederroedern (FR)

( * ) Notice: Subject to any disclaimer, the term of this patent is extended or adjusted under 35 U.S.C. 154(b) by 132 days.

(21) Appl. No.: 16/098,310

(22) PCT Filed: Apr. 28, 2017

(86) PCT No.: PCT/EP2017/060282
§ 371 (c)(1),
(2) Date: Nov. 1, 2018

(87) PCT Pub. No.: WO2017/191069
PCT Pub. Date: Nov. 9, 2017

(65) Prior Publication Data
US 2019/0159784 A1 May 30, 2019

(30) Foreign Application Priority Data
May 2, 2016 (FR) .................................... 16 53954

(51) Int. Cl.
*A61B 17/12* (2006.01)
*A61M 25/10* (2013.01)
(Continued)

(52) U.S. Cl.
CPC .... *A61B 17/12104* (2013.01); *A61B 17/1204* (2013.01); *A61B 17/12031* (2013.01);
(Continued)

(58) Field of Classification Search
CPC .......... A61B 17/1204; A61B 17/12031; A61B 17/12104; A61B 17/12136;
(Continued)

(56) References Cited

U.S. PATENT DOCUMENTS

2010/0241241 A1* 9/2010 McKnight ................ A61F 2/04
623/23.68
2012/0184808 A1 7/2012 Yang

FOREIGN PATENT DOCUMENTS

WO WO 2013/146210 A1 10/2013

OTHER PUBLICATIONS

Deprest, et al. 2004 "Fetoscopic tracheal occlusion (FETO) for severe congenital diaphragmatic hernia: evolution of a technique and preliminary results" *Ultrasound Obstet Gynecol* 24: 121-126.
(Continued)

*Primary Examiner* — Katherine H Schwiker
*Assistant Examiner* — Alexis D Amechi
(74) *Attorney, Agent, or Firm* — Knobbe, Martens, Olson & Bear, LLP

(57) ABSTRACT

The balloon includes a pouch formed of a sealed wall delimiting an internal space, and a valve for filling the internal space with a fluid, capable of being occluded after filling the internal space. The pouch delimits a fluid-draining orifice opening into the internal space. The balloon further
(Continued)

includes an occluding ball that occludes the draining orifice. The occluding ball can be spherical or polyhedral, and be capable of releasing the draining orifice under the effect of a magnetic field, so as to enable the at least partial drainage of the fluid contained in the internal space. The occluding ball is movable along at least two distinct axes in relation to the pouch.

19 Claims, 5 Drawing Sheets

(51) Int. Cl.
A61B 17/42 (2006.01)
A61B 17/00 (2006.01)

(52) U.S. Cl.
CPC ........ *A61B 17/12136* (2013.01); *A61B 17/42* (2013.01); *A61M 25/10* (2013.01); *A61M 25/10186* (2013.11); *A61B 2017/00411* (2013.01); *A61B 2017/00876* (2013.01); *A61B 2017/12054* (2013.01); *A61B 2503/02* (2013.01); *A61M 2025/1054* (2013.01); *A61M 2205/3317* (2013.01)

(58) Field of Classification Search
CPC .. A61B 2017/1205; A61B 2017/12054; A61B 2017/12086; A61B 2017/00876; A61B 17/42; A61M 25/10; A61M 2025/1054; A61M 2025/1018; A61M 2025/10184; A61M 2025/10185; A61M 2025/10186
See application file for complete search history.

(56) References Cited

OTHER PUBLICATIONS

Deprest, et al. 2005 "Fetal Intervention for Congenital Diaphragmatic Hernia: The European Experience" *Seminars in Perinatology*: pp. 94-103.
Deprest, et al. 2011 "Technical aspects of fetal endoscopic tracheal occlusion for congenital diaphragmatic hernia" *Journal of Pediatric Surgery* 46: 22-32.

* cited by examiner

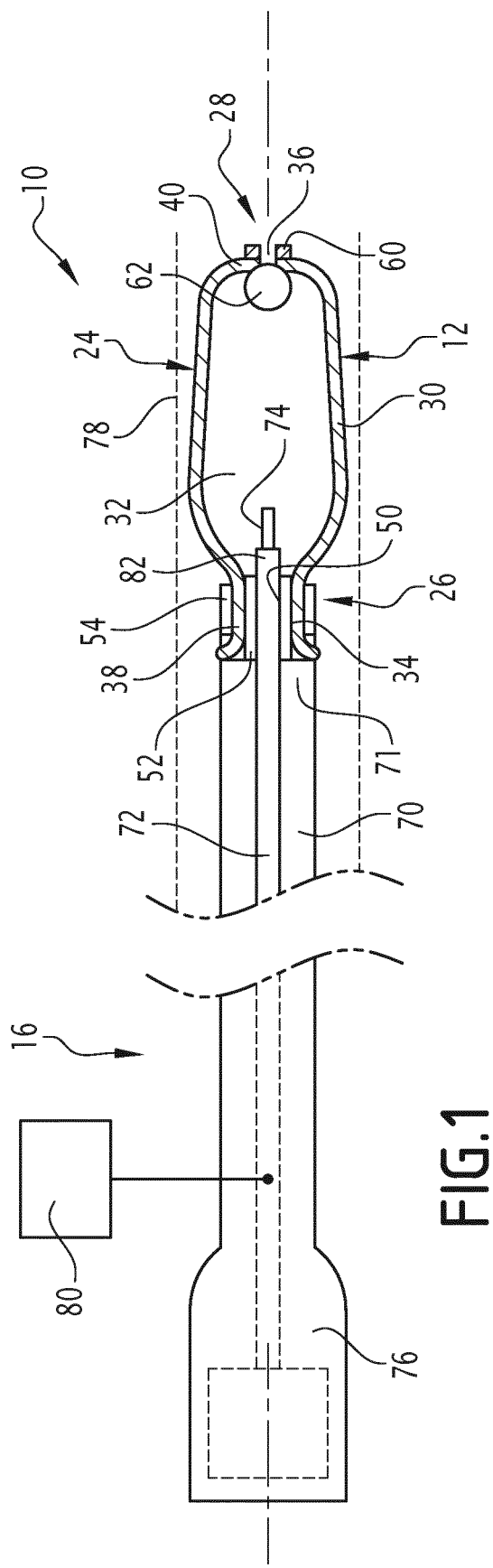
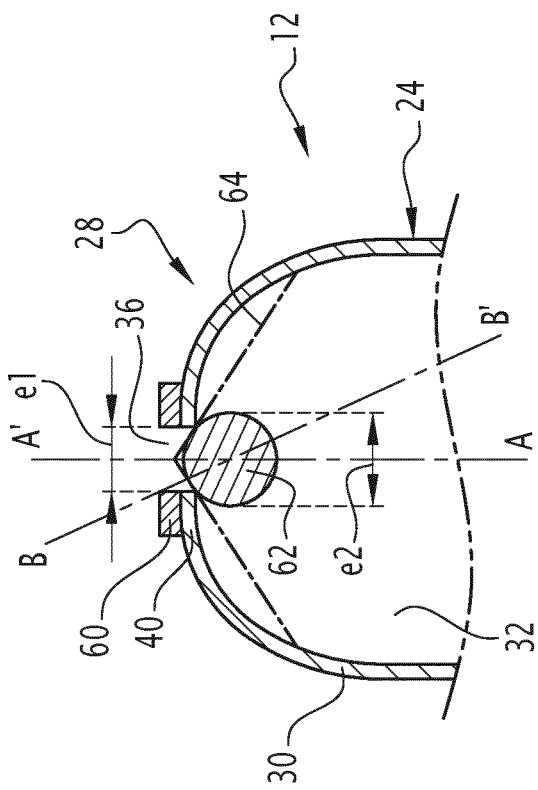
FIG.1
FIG.2

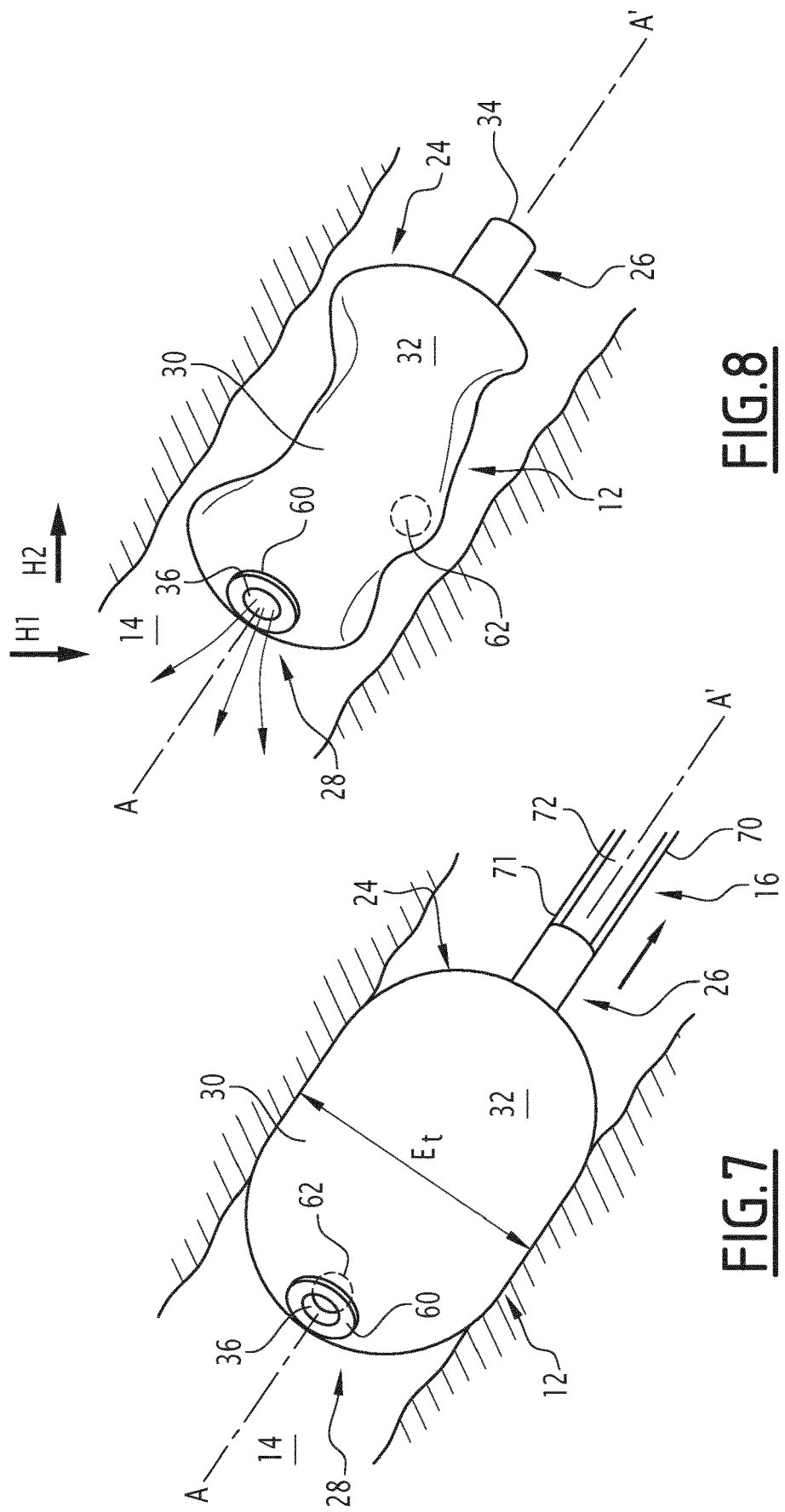

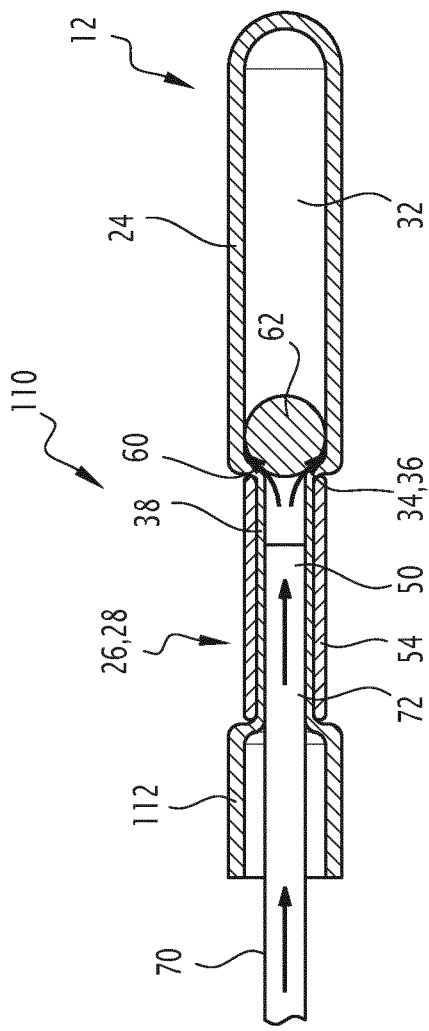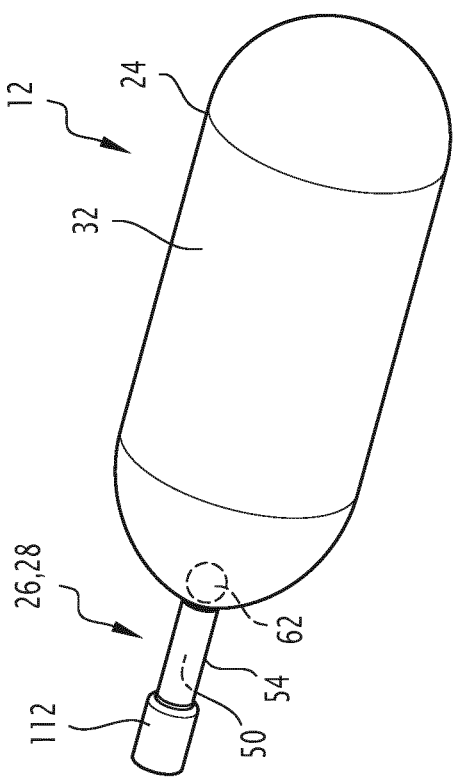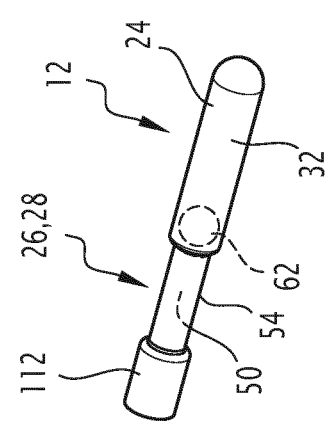

INFLATABLE AND DETACHABLE BALLOON, DESIGNED TO BE IMPLANTED IN A BODY CAVITY, ASSOCIATED TREATMENT KIT AND DRAINING METHOD

FIELD

The present invention relates to an inflatable balloon, designed to be implanted in a body cavity, comprising:
- a pouch formed of a sealed wall delimiting an internal space;
- a valve for filling the internal space with a fluid, capable of being occluded after filling the internal space.

BACKGROUND

The balloon is capable of being inserted into the end of a deployment device and of being detached from the device.

Such a balloon is designed specifically to be implanted in the trachea of a fetus in order to perform a fetal tracheal occlusion when the fetus is affected by a congenital diaphragmatic hernia. The balloon can also be used in the context of potential indications, such as the premature rupture of membranes or any other condition associated with a fetal pulmonary hypoplasia. A congenital diaphragmatic hernia is a condition that occasionally affects fetuses, with an incidence ranging from 1/3000 to 1/5000 among newborn babies.

This hernia results in an invasion of the organs of the abdomen, such as the intestine, stomach and/or the liver, into the thoracic cavity due to a diaphragmatic defect. This applies a pressure on the developing lungs and causes a pulmonary hypoplasia likely to lead to respiratory failure and sometimes even the death of the neonate. Current mortality resulting from an isolated congenital diaphragmatic hernia is estimated to be around 30% according to certain studies. Pulmonary hypoplasia is more or less severe depending on the size of the hernia. The consequences once the child is born are respiratory failure, but also pulmonary arterial hypertension.

In order to overcome this problem, it is known specifically from the article "Technical Aspects of Fetal Endoscopic Tracheal Occlusion for Congenital Diaphragmatic Hernia," Journal of Pediatric Surgery, (2011) 46, 22-32, to implant a balloon by endoscopy into the trachea of the fetus and to fill this balloon with fluid in order to block within the lungs pulmonary secretions upstream of the balloon resulting in a hypertension that stimulates pulmonary development.

SUMMARY

When this technique is applied, studies show a significant improvement in pulmonary development, considerably increasing the chances of survival of the newborn baby after birth.

To be effective, the implantation of a balloon in the trachea of a fetus must therefore block the natural airways of the fetus. It is, however, necessary to deflate the balloon, by performing another endoscopy or by piercing the wall of the balloon, in order to unblock the natural airways.

This operation is performed in utero at around 34 weeks of amenorrhea or beforehand if the waters break or at the start of labor. In fact, removal of the balloon before birth is crucial to achieve adequate cell maturation of the lungs, which increases the chances of neonatal survival. Removal in utero also facilitates neonatal management and, in certain cases, makes it possible to envisage a vaginal delivery.

Difficulties result from the fact that such an operation can only be performed by a specialized team, that this operation is not always technically achievable and that it is associated with a high perinatal morbimortality.

Moreover, there is always a risk that delivery occurs before the balloon can be deflated. This can have dramatic consequences for the newborn baby if the team in charge of the delivery fails to remove the balloon during labor or very soon after delivery.

Patients carrying a fetus having a balloon in the trachea are thus compelled to remain near or in a hospital center capable of performing such an intervention quickly and in the safest possible manner.

This is inconvenient and expensive if the patient does not live close to such a hospital center.

One object of the invention is to provide an inflatable balloon that is easy and practical to implant in a body cavity, particularly the trachea of a fetus, and that can nevertheless be simply deflated when desired.

To this end, the subject of the invention is a balloon of the above-mentioned type, characterized in that the pouch delimits a fluid-draining orifice opening into the internal space, the balloon comprising an element that occludes the draining orifice, the occluding element being capable of releasing the draining orifice under the effect of a magnetic field, so as to enable the at least partial drainage of the fluid contained in the internal space, the occluding element being movable along at least two distinct axes in relation to the pouch.

The balloon according to the invention can comprise one or more of the following characteristics, taken in isolation or in any technically possible combination:
- the occluding element is arranged in the internal space;
- the occluding element is freely movable in the internal space defined by the pouch under the effect of a magnetic field;
- the occluding element is capable of being held by magnetization in a position of occluding the draining orifice, the occluding element being capable of being moved away from the draining orifice under the effect of a magnetic field capable of overcoming the magnetization of the occluding element in the position of occluding the draining orifice;
- the balloon comprises a seat to retain the occluding element, arranged near the draining orifice, the occluding element cooperating by magnetization with the retaining seat in a position that occludes the draining orifice; the retaining seat preferably being a ring mounted on the sealed wall around the draining orifice;
- the retaining seat is coated with a layer of flexible material, the occluding element being arranged bearing on the layer of flexible material in a position that occludes the draining orifice;
- the occluding element is a ball;
- the occluding element is permanently magnetized;
- the occluding element is capable of being moved into at least two distinct positions of releasing the draining orifice on two intersecting axes passing through the draining orifice;
- the sealed wall of the pouch is made of a polymer chosen from silicone, latex, polyurethane and/or polyisoprene;
- the draining orifice is defined by the filling valve, the occluding element being capable of closing the filling valve after the internal space has been filled;
- the filling valve comprises a ring to guide a balloon-inflation tube, the guiding ring and/or the occluding element having a biocompatible coating.

The subject matter of the invention also relates to a patient treatment kit comprising:
- a balloon as described above;
- a balloon inflation and deployment device, comprising a balloon support guide, the balloon being mounted in a releasable manner on the support guide, and a balloon inflation tube, capable of being inserted in a releasable manner into the filling valve.

Another subject of the invention is a method of draining a balloon as defined above, the balloon being implanted in a body cavity, the internal space of the balloon containing a fluid, the occluding element occluding the draining orifice. The method comprising the following steps:
- subjecting the balloon to an external magnetic field, advantageously produced by a nuclear magnetic resonance machine, in at least one first direction;
- moving the occluding element along at least one axis under the effect of an external magnetic field in order to release the draining orifice;
- at least partially draining the fluid contained in the internal space through the draining orifice.

The method according to the invention can comprise one or more of the following characteristics, taken in isolation or in any technically possible combination:
- a step of subjecting the balloon to an external magnetic field, advantageously produced by the nuclear magnetic resonance machine, in at least one second direction, distinct from the first direction.

The invention relates more generally to a method of opening an orifice for draining a fluid in an implant, the implant comprising a member that occludes the draining orifice to enable the at least partial passage of the fluid present in the implant through the draining orifice, the method comprising the following steps:
- subjecting the implant to an external magnetic field originating from a nuclear magnetic resonance machine in at least one first direction;
- moving the occluding element along at least one axis under the effect of the external magnetic field, in order to release the draining orifice;
- passing fluid through the draining orifice.

The opening method can comprise a step of subjecting the implant to the external magnetic field produced by the nuclear magnetic resonance machine, in at least one direction, distinct from the first direction.

The invention also relates to a method of surgical treatment comprising the following steps:
- supplying a kit as described above;
- placing, advantageously by endoscopy, the balloon in a body cavity, with the aid of the deployment and inflation device;
- inflating the balloon in the body cavity;
- deploying the balloon in the body cavity and removing the inflation and deployment device from the body cavity.

The surgical treatment method can comprise the following characteristic:
- the placing step involves conveying the balloon into the amniotic cavity of a patient, then inserting it into the trachea of a fetus present in the amniotic cavity.

BRIEF DESCRIPTION OF THE DRAWINGS

A better understanding of the invention will emerge from the following description, given purely by way of example, and made with reference to the accompanying drawings, in which:

FIG. 1 is a schematic view of a first treatment kit according to the invention, before implantation of the balloon in a body cavity;

FIG. 2 is a detail showing the draining orifice of the balloon in an occluding position, seen from inside the balloon;

FIG. 7 is a perspective view of the inflated balloon, during its deployment;

FIG. 8 is a view similar to that of FIG. 7, during the movement of the balloon-occluding element in order to release the draining orifice, under the effect of a magnetic field external to the patient;

FIG. 9 is a front perspective three-quarter view of a second balloon according to the invention, before its inflation;

FIG. 10 is a cross-sectional view along a median axial plane of the balloon of FIG. 9, during its inflation;

FIG. 11 is a view similar to FIG. 9, after inflation of the balloon;

DETAILED DESCRIPTION

A first treatment kit 10 according to the invention is shown schematically in FIG. 1.

Figure 6:
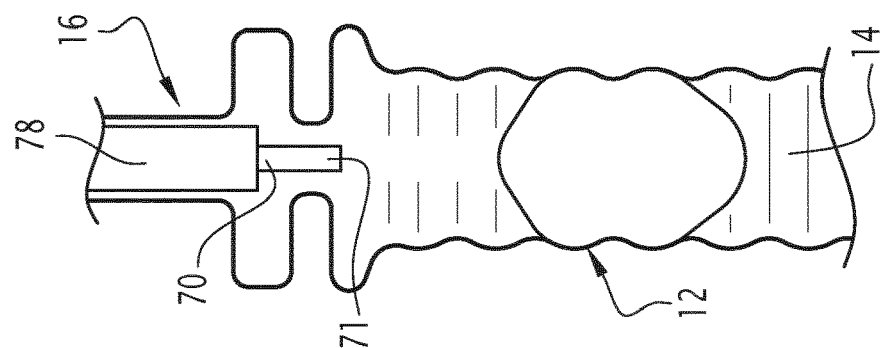
FIGS. 3 to 6 show the successive steps of introducing the balloon in the body cavity.
Figure 5:
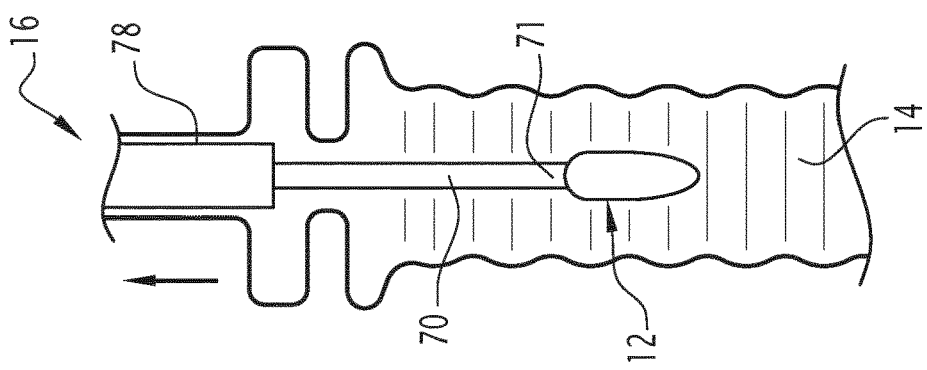
Figure 4:
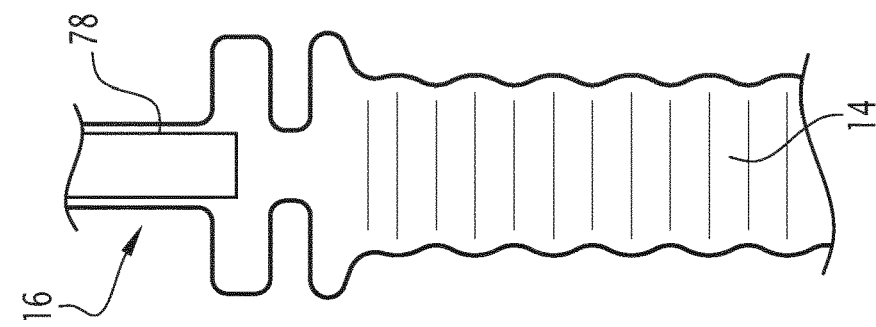

The treatment kit 10 comprises an inflatable balloon 12 according to the invention, designed to be implanted in a body cavity 14, shown in FIGS. 4 to 6. The kit 10 also comprises a device 16 for the inflation and deployment of the inflatable balloon 12 into the cavity 14, shown in particular in FIGS. 1 and 3.

In the particular application shown in FIGS. 3 to 6, the cavity 14 is the trachea of a fetus 18, present in the amniotic cavity 20 of a patient 22. The fetus 18 suffers for example from a congenital diaphragmatic hernia.

With reference to FIGS. 1 and 2, the balloon 12 comprises a pouch 24 that can be inflated by a fluid, a valve 26 for filling the pouch 24 and, according to the invention, a draining valve 28 that can be released under the effect of a magnetic field external to the patient 22. The draining valve 28 is distinct from the filling valve 26.

The pouch 24 is formed of a sealed wall 30 that is deformable to the touch, delimiting an internal space 32 of variable volume depending on the quantity of fluid that it contains.

The sealed wall 30 is made, for example, from a polymer material such as silicone or latex or from a rubber such as polyisoprene.

The thickness of the sealed wall 30 is less than 1 mm and is usually between 0.1 mm and 0.5 mm.

The pouch 24 usually has an elongated shape along an axis A-A', shown in FIG. 2.

With reference to FIG. 1, the pouch 24 defines an orifice 34 for filling the internal space 32, occluded selectively by the filling valve 26, and a draining orifice 36, distinct from the filling orifice 34, occluded selectively by the draining valve 28.

In this example, the filling orifice 34 is located at a proximal end of the pouch 24, taken along the axis A-A'. The orifice 34 is delimited at its periphery by a mounting sleeve 38 of the valve 26 projecting along the axis A-A' in relation to the wall 30. The sleeve 38 forms one piece with the wall 30.

The draining orifice 36 passes through a distal peripheral region 40 of the wall 30, located opposite the filling orifice 34 in this example.

The transverse extension of the draining orifice 36 is advantageously less than 1.5 mm and ranges between 1 mm and 1.5 mm, for example.

The internal space 32 of the pouch 24 is capable of being filled by a fluid, preferably by a liquid, through the filling valve 26, in order to change the pouch 24 from a deflated configuration, contracted radially (shown in FIG. 1 or FIG. 5) to an inflated configuration, dilated radially (shown in FIG. 7).

In the deflated configuration, the pouch 24 advantageously has a maximum transverse extension which, taken perpendicular to the axis A-A', is advantageously less than 1.5 mm and usually ranges between 1 mm and 1.5 mm.

The length of the pouch 24, taken along the axis A-A', is advantageously between 5 mm and 10 mm.

The volume of the internal space 32 therefore advantageously ranges between 3 mm$^3$ and 10 mm$^3$.

In the inflated configuration, the pouch 24 advantageously has a maximum transverse extension Et, taken perpendicular to the axis A-A', advantageously less than 10 mm and ranging, for example, between 5 mm and 9 mm.

The length of the pouch 24 in the inflated configuration, taken along the axis A-A', exceeds the length of the pouch 24 in the deflated configuration. This length advantageously ranges between 15 mm and 25 mm.

The volume of the internal space 32 therefore advantageously ranges between 250 mm$^3$ and 1600 mm$^3$.

The inflation fluid of the pouch is for example a liquid, specifically a physiological liquid. This liquid may contain a contrast agent capable of being visible by radiography.

With reference to FIG. 1, the filling valve 26 is normally closed. It defines a central lumen 50 for the injection of fluid into the internal space 32.

In this example, the filling valve 26 projects axially in relation to the wall 30. It is fitted around the sleeve 38.

It comprises, inside the sleeve 38, a deformable annular seal 52 defining the central lumen 50, and a peripheral ring 54 fitted around the sleeve 38 to clamp the sleeve 38 and the seal 52.

The annular seal 52 is arranged in the filling orifice 34. It is radially deformable by compression, to enable the introduction of an element to fill the internal space 32. It is capable of returning spontaneously to a configuration that occludes the filling orifice 34.

With reference to FIG. 2, the draining valve 28 comprises a seat 60 fixed to the sealed wall 30, in the peripheral region 40 around the draining orifice 36, and an element 62 that occludes the draining orifice 36, movable along at least two distinct axes A-A' and B-B', under the effect of a magnetic field external to the patient 22.

In this example, the seat 60 is mounted on the peripheral region 40, on the outside of the sealed wall 30. It is for example glued to the peripheral region 40.

Here, the seat 60 has an annular shape surrounding the draining orifice 36.

The seat 60 is made using a ferromagnetic metal material, capable of being magnetized by a permanent magnet.

The occluding element 62 is here arranged in the internal space 32. As shown in FIG. 2, it has a maximum transverse extension e2 that exceeds the maximum transverse extension e1 of the draining orifice 36. In this example, the occluding element 62 is a ball.

The occluding element 62 is permanently magnetized. It is thus capable of cooperating magnetically with the seat 60 so as to be held in a position that occludes the draining orifice 36, into which it is applied against the peripheral region 40 facing the seat 60.

In this position, the occluding element 62 totally occludes the orifice 36 and prevents the passage of fluid from the internal volume 32 towards the outside of the pouch 24.

The sealing around the draining orifice 36 is enhanced by the presence of the peripheral region 40, on which bears the occluding element 62, which forms a deformable intermediate layer.

Under the effect of an external magnetic field, capable of creating a force to attract the occluding element 62 greater than the cooperation force between the occluding element 62 and the seat 60, the occluding element 62 is capable of moving away from the draining orifice 36 into the internal space 32 along at least two axes A-A', B-B'.

The intensity of the magnetic field capable of releasing the occluding element 62 is for example greater than 0.1 T and ranges specifically between 0.5 T and 2 T.

In practice, when it detaches from the occluding position, the occluding element 62 is capable of moving freely along a multitude of axes in a cone 64 centered on axis A-A' of the draining orifice 36, at the orifice 36. The cone 64 has an angle opening towards the internal space 32 greater than 30°, preferably greater than 90°, and advantageously equal to 180°.

No mechanical retaining means connect the occluding element 62 to the inflatable pouch 24 and/or to the seat 60.

Once detached from the occluding position, the occluding element 62 is capable of reaching at least one position of release of the orifice 36, this position depending on the orientation of the patient 22, and that of the external magnetic field.

In particular, the occluding element 62 is capable of occupying a plurality of distinct release positions, within the internal space 32, after having left the occluding position, one of which is shown in FIG. 8.

Figure 3:
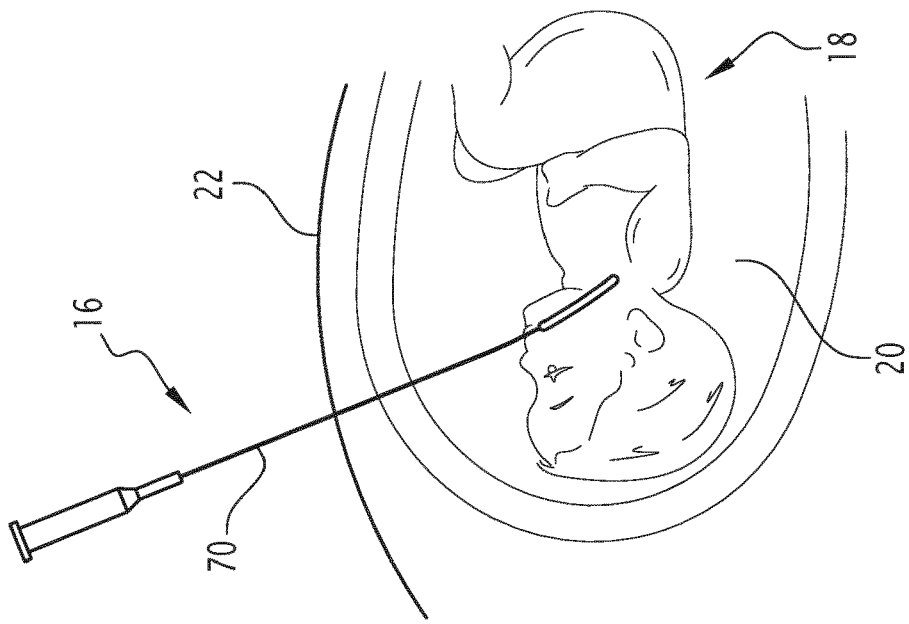

With reference to FIGS. 1 and 3, the device 16 for inflating and deploying the balloon 12 comprises a flexible guide 70 carrying at its distal end 71 the balloon 12, an inflation tube 72 arranged in the guide 70 and, advantageously, a mandrel rod 74 arranged in the inflation tube 72 to stiffen it.

The device 16 also comprises a proximal end-piece 76 so that it can be manipulated by a physician and, advantageously, a removable sheath 78 to protect the balloon 12.

The guide 70 extends between the proximal end-piece 76 and the distal end 71. It is capable of being deformed in order to be introduced into the patient 22, advantageously by endoscopy, and to reach the cavity 14.

The inflation tube 72 extends through the guide 70. It is connected upstream to a container 80 for the injection of fluid.

The inflation tube 72 has a distal part 82 that projects in relation to the distal end 71 of the guide 70 so as to be introduced into the central lumen 50 of the filling valve 26.

The removable sheath 78 is capable of covering the balloon 12 during its introduction into the cavity 14. It is longitudinally movable around the guide 70 in order to uncover the balloon 12, at its point of implantation in the cavity 14.

The operation of the treatment kit 10 within the context of an implantation in a body cavity 14 will now be described.

This implantation is for example made in the trachea of a fetus 18 present in the amniotic cavity 20 of a patient 22.

Initially, the balloon 12 is fitted to the distal end 71 of the guide 70 of the inflation and deployment device 16. The distal part 82 of the inflation tube 72 is introduced into the filling valve 26, by radial deformation of the annular seal 52.

The occluding element 62 is pressed onto the seat 60 against the peripheral region 40. It occupies its position of occluding the orifice 36.

The pouch 24 then occupies its deflated configuration, of minimum radial extension, shown in FIGS. 1 and 5.

The device 16, provided with the balloon 12 at its end is then introduced into the patient 22, by endoscopy. In the example shown in FIG. 3, the physician introduces it into the amniotic cavity 20, then pushes it through the airways of the fetus 18 until it reaches the trachea, passing through the vocal cords (FIG. 4).

Once the distal end 71 is in the cavity 14, the physician extracts the balloon 12 from the sheath 78, by pulling the sheath towards the proximal end-piece 76, as shown in FIG. 5.

The inflatable pouch 24 still occupies its deflated configuration.

The physician then injects inflation fluid into the internal space 32 through the inflation tube 72 introduced into the filling valve 26. The pouch 24 dilates radially to reach its inflated configuration, bearing on the wall delimiting the cavity 14, as shown in FIG. 6.

The physician then detaches the balloon 12 from the inflation and deployment device 16, by extracting the inflation tube 72 from the filling valve 26. The filling valve 26 re-closes by radial dilation of the annular seal 52.

The physician then removes the device 16 from the patient 22.

During and after inflation, the occluding element 62 remains confined within the internal volume 32.

The cavity 14 is then occluded. In the case of a fetus 18 suffering from a congenital diaphragmatic hernia, the pulmonary development of the fetus is improved, thanks to the presence of the inflated balloon 12 in the trachea.

When the balloon 12 must be removed, the patient is subjected to a high-intensity external magnetic field, for example of an intensity exceeding 0.1 T.

This magnetic field is produced, for example, by a magnetic resonance imaging machine. Depending on circumstances, the patient positions herself inside the machine during an image acquisition or preferably without image acquisition in the machine. Preferably, the patient need not position herself inside the machine, since the leakage field of the machine when switched on or at the entrance of the tunnel is advantageously sufficient to produce an adequate magnetic field to release the occluding element 62, in which case the patient simply stands in front of the machine.

Preferably, as shown in FIG. 8, the relative orientation between the magnetic field and the patient 22 is modified, for example by moving the patient, so that the magnetic field is applied along at least two distinct axes H1 and H2, as shown in FIG. 8.

The external magnetic field creates an attraction force on the occluding element 62 that overcomes the cooperation force between the occluding element 62 and the seat 60.

Under the effect of the external magnetic field, the occluding element 62 moves away from the draining orifice 36 to a position in which the orifice 36 is released, as shown for example in FIG. 8.

At least some of the fluid present in the internal space 32 then flows from the internal space towards the outside through the draining orifice 36, causing the rapid deflation of the balloon 12.

The airways of the fetus are then clear again. The balloon 12 is then capable of being expelled from the fetus by the release of pulmonary fluid under pressure or is removed a few days after birth.

The release of the occluding element 62 is immediate and very easy to achieve. As no mechanical connection exists between, on the one hand, the occluding element 62 and, on the other, the inflatable pouch 24 or the seat 60, this release is very reliable and does not depend on a mechanical or electrical mechanism. By contrast, the clearance of the draining orifice 36 is caused solely by the external magnetic field applied, combined with the forces of gravity being applied on the occluding element 62.

Furthermore, this release is non-invasive for the patient 22 since it can be performed remotely with no need to incise the patient or even penetrate the amniotic cavity 20.

The draining valve 28 thus obtained is inexpensive to produce, whilst ensuring proper functioning, whatever the circumstances.

The risks for the fetus 18 are therefore totally removed since the withdrawal of the balloon 12 is facilitated by its immediate deflation, and its expulsion from the trachea, at the desired moment and with no invasive procedure.

The patient 22 benefits from an appropriate treatment, ensuring the proper development of her fetus 18, without necessarily being compelled to remain within the vicinity of or stay at a specialized hospital center, which limits costs while maintaining the quality of care.

A second treatment kit 110 according to the invention is shown in FIGS. 9 to 13.

The balloon 12 of the second kit 110 is formed in a similar manner to the balloon 12 of the first kit 10. In particular, the dimensions of the balloon 12 of the second kit 110 are the same as those of the balloon 12 of the first kit 10.

However, unlike the first kit 10, the balloon 12 comprises a single valve forming both a filling valve 26 and a draining valve 28.

The draining orifice 36 is formed by the filling orifice 34 at the end of the valve 26, 28. The pouch 24 is therefore provided with a single orifice 34, 36 enabling the filling of the internal space 32 with fluid and the draining of the fluid contained in the internal space 32.

The occluding element 62 occludes, by default, the filling valve 26. Thus the peripheral ring 54 delimiting the filling valve 26 has no annular seal. It therefore defines a central lumen 50 that is permanently clear.

As with the balloon 12 of the first kit 10, the pouch 24 is extended by a sleeve 38 inserted in the peripheral ring 54 and delimiting the periphery of the central lumen 50.

In this example, the sleeve 38 is extended beyond the ring 54, opposite the pouch 24, by an annular end-piece 112 opening to the outside.

The peripheral ring 54 is here made of a ferromagnetic metallic material. It defines the seat 60, on which the occluding element 62 bears in the occluding position, in the peripheral region 40.

Here the occluding element 62 is permanently magnetized. At rest, it therefore applies against the seat 60 in the occluding position.

The operation of the second kit 110 according to the invention is similar to that of the first kit 10.

However, unlike the first kit 10, the inflation tube 72 is introduced into the peripheral ring 54 of the filling valve 26, without opening the filling orifice 34, since the occluding element 62 stays applied against the seat 60.

As shown in FIG. 10, the hydraulic force generated by the pressure of the fluid injected by the inflation tube 72 pushes the occluding element 62 away from the seat 60 and at least partially overcomes the magnetic force holding the occluding element 62 against the seat 60.

A gap therefore forms between the seat 60 and the occluding element 62 allowing fluid to enter the internal space 32 and the pouch 24 to inflate.

When inflation has been completed, the occluding element 62 resumes its occluding position under the effect of the magnetic force. The internal space 32 of fluid is occluded in a sealed manner, as shown in FIG. 11. An induced pressure, for example exceeding 0.5 relative bars, and specifically on the order of 1 relative bar, exists in the internal space 32 of the balloon 12.

This pressure is necessary to begin inflation (triggering the elasticity of the balloon 12). This pressure drops in the second phase of inflation. The induced pressure depends on the elasticity of the material, the wall thickness, the initial length of the balloon, etc. It enhances the sealing of the valve. In order to deflate the balloon 12, the patient is subjected to a high-intensity external magnetic field, as previously described.

Figure 12:
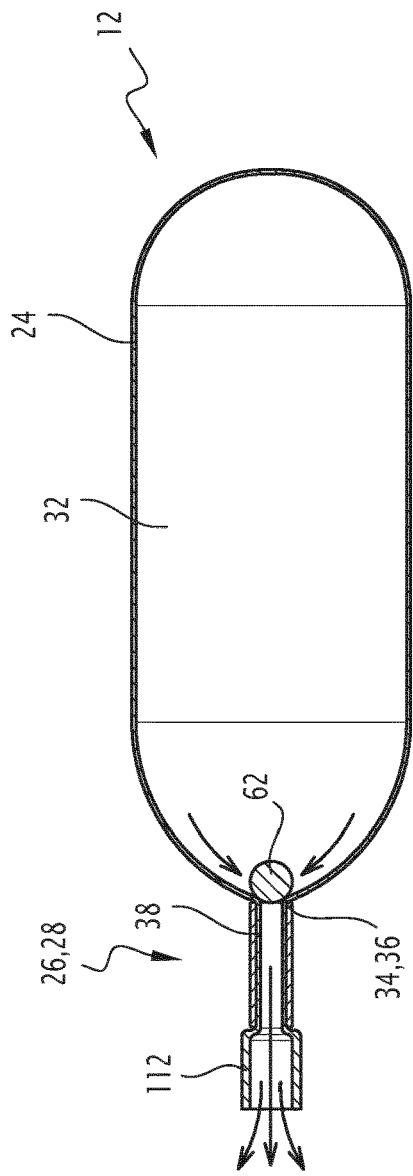
FIG. 12 is a view similar to FIG. 10, during deflation.

As shown in FIG. 12, this causes the release of the occluding element 62, at least temporarily, away from the seat 60 and the passage of fluid around the occluding element 62 towards the central lumen 50 so as to deflate the pouch 24.

The movement of the occluding element 62 away from the seat 60 is advantageously very limited, for example limited to a few hundredths or even a few tenths of a millimeter.

The occluding element 62 is movable, however, along at least two distinct axes in relation to the pouch 24, as with the balloon 12 of the first kit 10, which does not require the orientation of the magnetic field to be controlled in a specific direction in order to release the occluding element 62.

Advantageously, for each of the balloons 12 described previously, the occluding element 62 and/or the peripheral ring 54 are provided with a biocompatible coating 114.

This coating is for example a coating of titanium, carbon, fluorinated polymer (specifically polytetrafluoroethylene), and/or parylene. As a variation, the coating is a film, specifically a polymer film, made for example of polyisoprene or polyurethane.

Figure 13:
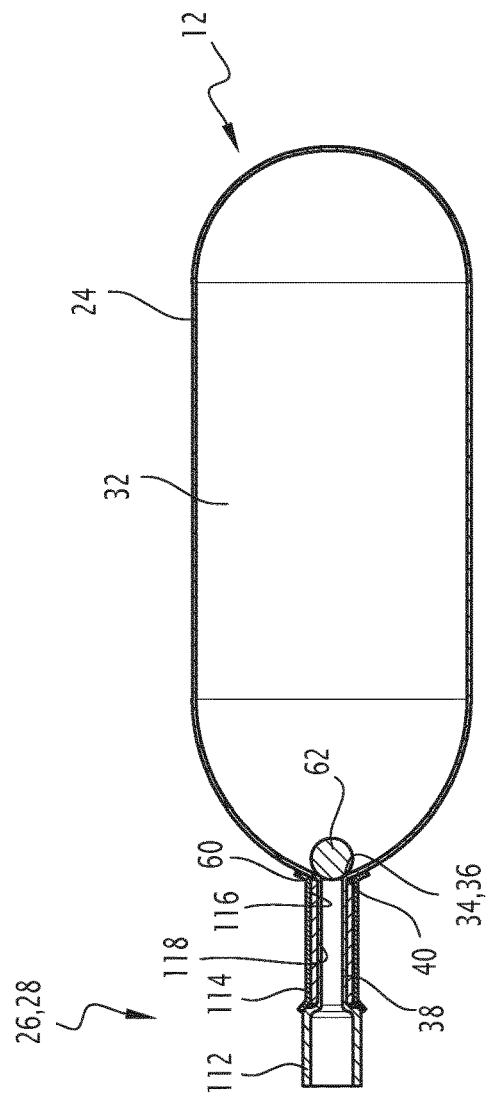
FIG. 13 is a view similar to FIG. 12 of a third balloon according to the invention.

In the example shown in FIG. 13, at least one external peripheral surface 116 of the ring 54 is provided with a biocompatible coating. Advantageously, an internal peripheral surface 118 of the ring 54 and the external surface of the occluding element 62 are also provided with this coating.

Figure 14:
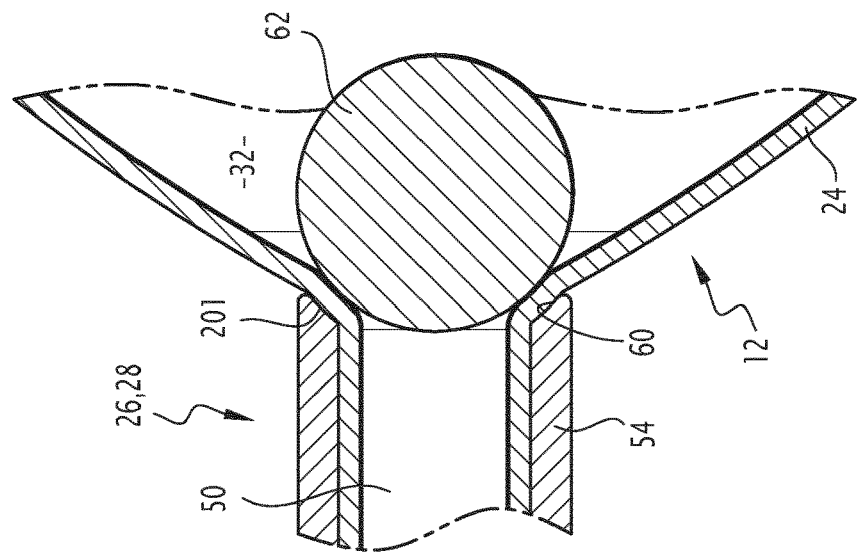
FIG. 14 is a detailed view of a variation of the balloon according to the invention.

In yet another variation, shown in FIG. 14, the ring 54 has a chamfer 201 at its end forming the seat 60 of the occluding element 62.

The occluding element 62 is thus capable of entering further into the internal diameter of the ring 54. This increases the contact surface and therefore the seal between the occluding element 62 and the ring 54, taken at the seat 60.

In another variation (not shown), the occluding element 62, after having left the occluding position, is not necessarily able to move freely within the entire internal space 32 but only within a limited region of the internal space 32. For example, a compartment for receiving the occluding element 62 is mounted within the internal space 32 around the draining orifice 36.

In another variation (not shown) the occluding element 62 is arranged in its occluding position outside the internal space 32. A compartment for receiving the occluding element 62 is mounted on the pouch 24, to the outside thereof, around the draining orifice 36. This receiving compartment is preferably perforated to allow the fluid from the internal space 32 to flow through it.

In other variations, the occluding element 62 is not spherical in shape but is of a different shape, for example polyhedral.

What is claimed is:

1. An inflatable balloon, designed to be implanted in a body cavity, comprising:
   a pouch formed of a sealed wall delimiting an internal space;
   a valve configured to fill the internal space with a fluid, wherein the valve is capable of being occluded after the internal space is filled;
   wherein the pouch delimits a fluid-draining orifice opening into the internal space, the balloon comprising an occluding ball that occludes the fluid-draining orifice, the occluding ball being capable of releasing the fluid-draining orifice under the effect of a magnetic field, so as to enable at least partial drainage of the fluid contained in the internal space, the occluding ball being movable along at least two distinct axes in relation to the pouch.

2. The balloon according to claim 1, wherein the occluding ball is arranged in the internal space.

3. The balloon according to claim 2, wherein the occluding ball is freely movable in the internal space defined by the pouch under the effect of the magnetic field.

4. The balloon according to claim 1, wherein the occluding ball is capable of being held by magnetization in a position of occluding the fluid-draining orifice, the occluding ball being capable of being moved away from the fluid-draining orifice under the effect of a second magnetic field capable of overcoming the magnetization holding the occluding ball in the position of occluding the fluid-draining orifice.

5. The balloon according to claim 1, comprising at least one retaining seat to retain the occluding ball, arranged near the fluid-draining orifice, the occluding ball cooperating by magnetization with the at least one retaining seat in a position that occludes the fluid-draining orifice.

6. The balloon according to claim 5, wherein the at least one retaining seat is coated with a layer of flexible material, the occluding ball being arranged bearing on the layer of flexible material in the position that occludes the fluid-draining orifice.

7. The balloon according to claim 5, wherein the at least one retaining seat is a ring mounted on the sealed wall around the fluid-draining orifice.

8. The balloon according to claim 1, wherein the occluding ball is spherical in shape.

9. The balloon according to claim 1, wherein the occluding ball is permanently magnetized.

10. The balloon according to claim 1, wherein the occluding ball is capable of being moved into at least two distinct positions of releasing the fluid-draining orifice on two intersecting axes passing through the fluid-draining orifice.

11. The balloon according to claim 1, wherein the sealed wall of the pouch is made of a polymer chosen from silicone, latex, polyurethane and/or polyisoprene.

12. The balloon according to claim 1, wherein the fluid-draining orifice is defined by the valve, the occluding ball being capable of closing the valve after the internal space has been filled.

13. The balloon according to claim 1, wherein the filling valve comprises a guiding ring to guide a tube for inflating the balloon, the guiding ring and/or the occluding ball having a biocompatible coating.

14. The balloon according to claim 1, wherein the occluding ball is polyhedral in shape.

15. A patient treatment kit comprising:
the balloon according to claim 1;
a balloon inflation and deployment device, comprising a balloon support guide, the balloon being mounted in a releasable manner on the support guide, and a balloon inflation tube, capable of being inserted in a releasable manner into the filling valve.

16. A method of draining the balloon according to claim 1, the balloon being implanted in a body cavity, the internal space of the balloon containing the fluid, the occluding ball occluding the fluid-draining orifice, the method comprising:
subjecting the balloon to an external magnetic field, in at least one first direction (H1);
moving the occluding ball along at least one axis under the effect of the external magnetic field in order to release the fluid-draining orifice;
at least partially draining the fluid contained in the internal space through the fluid-draining draining orifice.

17. The method according to claim 16, further comprising subjecting the balloon to a second external magnetic field, in at least one second direction (H2), distinct from the first direction (H1).

18. The method according to claim 16, wherein the external magnetic field, in the first direction, is produced by a nuclear magnetic resonance machine.

19. The method according to claim 17, wherein the second external magnetic field, in the second direction, is produced by a nuclear magnetic resonance machine.

* * * * *